United States Patent [19]

Wegener et al.

[11] Patent Number: 4,931,568

[45] Date of Patent: Jun. 5, 1990

[54] PROCESS FOR THE PREPARATION OF THIOPHENE ETHERS

[75] Inventors: Peter Wegener, Königstein; Michael Feldhues, Bad Soden am Taunus; Heinz Litterer, Bad Schwalbach, all of Fed. Rep. of Germany

[73] Assignee: Hoechst Aktiengesellschaft, Frankfurt am Main, Fed. Rep. of Germany

[21] Appl. No.: 308,893

[22] Filed: Feb. 9, 1989

[30] Foreign Application Priority Data

Feb. 13, 1988 [DE] Fed. Rep. of Germany ....... 3804522

[51] Int. Cl.$^5$ .................. C07D 409/00; C07D 333/32
[52] U.S. Cl. .......................................... 549/6; 549/62; 549/65; 549/66
[58] Field of Search .......................... 549/62, 6, 65, 66; 568/630

[56] References Cited

U.S. PATENT DOCUMENTS 4,579,980  4/1986  Kogoma et al. .................... 568/630

OTHER PUBLICATIONS

Jakobsen, Chem. Abst., vol. 64, (1966), 9659c.

*Primary Examiner*—Alan Siegel

[57] ABSTRACT

Thiophene ethers having relatively large side chains can be easily obtained by reacting 2-, 3-, 2,3-, 2,4- or 3,4-$C_1$-$C_3$-alkoxythiophenes in the presence of an acid catalyst with a compound containing an OH group. The novel thiophene ethers are suitable as monomers for electrically conducting polymers.

8 Claims, No Drawings

PROCESS FOR THE PREPARATION OF THIOPHENE ETHERS

The present invention relates to a simplified process for the preparation of thiophene ethers and the compounds obtained by this process.

Thiophenes which are substituted in the 3-position or 3,4-position can be converted into electrically conduction polymers by oxidation. Compared to unsubstituted thiophene, 3-alkylthiophenes are distinguished by an oxidation potential which is more favorable for polymerization, since it is lower, and the polymers prepared therefrom by higher stability.

Further reduction of the oxidation potential by about 0.4 V is achieved by substitution by a 3-methoxy group. The preparation of 3-methoxythiophene is known; it is carried out by reaction of 3-bromothiophene with sodium methylate in very high yield. However, thiophene ethers having larger radicals cannot be prepared in this manner, in particular not if the alcohols to be used contain additional active atoms or active groups.

It has been found that thiophene ethers having larger side chains can be easily produced by reaction $C_1$–$C_3$-alkoxythiophenes with compounds containing OH groups in the presence of an acid.

The invention accordingly relates to a process for the preparation of thiophene ethers of the formula I

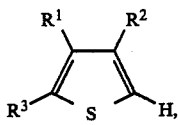

(I)

in which
$R^1$ denotes a straight-chain or branched $C_1$–$C_{18}$-alkoxy radical, a $C_3$–$C_{18}$-alkenyloxy radical, a $C_3$–$C_{12}$-alkynyloxy radical, a $C_5$–$C_6$-cycloalkoxy radical, a phenyl-$C_1$–$C_4$-alkoxy radical, a radical of the formula II

(II)

in which n denotes 2 to 6 and X denotes a halogen atom, a hydroxyl, carboxylic ester, —$SO_3Me$ (Me is an alkali metal or 'N+$R_4^5$ where $R^5$ H, is alkyl), nitro, cyano, carboxamide, —$OCH_3$, —$OC_2H_5$ or —(OCH$_2$CH$_2$)$_m$— OCH$_3$ group where m is 1 to 3, a quaternary ammonium group or a —$P(O)(OR^4)_2$ group where $R^4$ is H or $C_1$–$C_4$-alkyl, or denotes a radical of glycolic acid, thioglycolic acid, lactic acid or the ester of these acids, $R^2$ denotes $R^1$ or a hydrogen atom, a $C_1$–$C_{12}$-alkyl group or an aryl radical, or $R^1$ and $R^2$, together with the carbon atoms linking them, form a five- to six-membered ring, and $R^3$ denotes a hydrogen atom, a $C_1$–$C_6$-alkyl group or a $C_4$–$C_6$-alkoxy group, which comprises heating a 2-, 3-, 2,3-, 2,4- or 3,4-$C_1$–$C_3$-alkoxythiophene together with a compound containing an OH group of the formula III

$R^1$—OH (III)

in which $R^1$ has the abovementioned meaning, in the presence of an acid catalyst in an amount of 1 to 10 mol %, relative to the amount of the alkoxythiophene, for 50 to 300 minutes to a temperature of 70° to 180° C. and separated off the resulting $C_1$–$C_3$-alcohol.

The invention further relates to thiophene ethers of the formula I

(I)

in which
$R^1$ denotes a straight-chain or branched $C_7$–$C_{18}$-alkoxy radical, a $C_4$–$C_{18}$-alkenyloxy radical, a $C_3$–$C_{12}$-alkynyloxy radical, a $C_5$–$C_6$-cycloalkoxy radical, a phenyl-$C_1$–$C_4$-alkoxy radical, a radical of the formula II

—O(CH$_2$)$_n$—X (II)

in which n is 2 to 6 and X denotes a halogen atom, a hydroxyl, carboxylic ester, —$SO_3Me$ (Me is an alkali metal or —N+$R_4^5$ where $R^5$ is H or alkyl), nitro, cyano, carboxamide, —$OCH_3$, —$OC_2H_5$ or —(OCH$_2$CH$_2$)$_m$— OCH$_3$ group where m is 1 to 3, a quaternary ammonium group or a —$P(O)(OR^4)_2$ group where $R^4$ is H or $C_1$–$C_4$-alkyl, or denotes a radical of glycolic acid, thioglycolic acid, lactic acid or the ester of these acids, $R^2$ denotes $R^1$ or a hydrogen atom, a $C_1$–$C_{12}$-alkyl group or an aryl radical, or $R^1$ and $R^2$, together with the carbon atoms linking them, form a five- to six-membered ring and $R^3$ denotes a hydrogen atom, a $C_1$–$C_6$-alkyl group or a $C_4$–$C_6$-alkoxy group.

The thiophene ethers prepared according to the invention are compounds of the formula I

(I)

in which
$R^1$ denotes a straight-chain or branched $C_1$–$C_{18}$-alkoxy radical, preferably a $C_7$–$C_{18}$-alkoxy radical, in particular a $C_{10}$–$C_{14}$-alkoxy radical, a $C_3$–$C_{18}$-alkenyloxy radical, preferably a $C_4$–$C_{18}$-alkenyloxy radical, a $C_3$–$C_{12}$-alkynyloxy radical, preferably a $C_3$–$C_8$-alkynyloxy radical, a $C_5$–$C_6$-cycloalkoxy radical, preferably a $C_6$-cycloalkoxy radical, a phenyl-$C_1$–$C_4$-alkoxy radical, a radical of the formula II

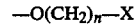

—O(CH$_2$)$_n$—X (II)

in which n is 2 to 6 and X denotes a halogen atom, a hydroxyl, carboxylic ester, —$SO_3Me$ (Me is an alkali metal or —N+$R_4^5$ where $R^5$ is H or alkyl), nitro, cyano, carboxamide, —$OCH_3$, —$OC_2H_5$, or a —(OCH$_2$CH$_2$)$_m$OCH$_3$ radical where m is 1 to 3, a quaternary ammonium group or a —$P(O)(OR^4)_2$ group where $R^4$ is H or $C_1$–$C_4$-alkyl, or denotes a radical of glycolic acid, thioglycolic acid, lactic acid or the ester of these acids.

R² denotes R¹ or a hydrogen atom, a $C_1$–$C_{12}$-alkyl group, preferably a $C_1$–$C_4$-alkyl group, or denotes an aryl radical, or R¹ and R², together with the carbon atoms linking them, form a five- to six-membered ring. Preferably R² is a hydrogen atom or a methyl group.

R³ denotes a hydrogen atom, a $C_1$–$C_4$-alkyl group, preferably a methyl group, or a $C_4$–$C_6$-alkoxy group.

For the process according to the invention, a 2-, 3-, 2,3-, 2,4-, or 3,4-$C_1$–$C_3$-alkoxythiophene is used, for example 3-methoxythiophene, 3-ethoxythiophene, 3-propoxythiophene, 3-methoxy-4-ethylthiophene and 3-methoxy-4-butylthiophene.

Preferably, methoxythiophenes are used. The $C_1$–$C_3$-alkoxythiophenes are reacted with a compound containing an OH group of the formula (III)

$$R^1\text{—OH} \qquad (III)$$

in which R¹ has the abovementioned meaning.

Examples of such compounds are straight-chain or branched $C_2$–$C_{18}$-alcohols, $C_3$–$C_{18}$-olefinic alcohols, $C_3$–$C_{12}$-acetylenic alcohols, cyclopentanol, cyclohexanol, phenylethyl alcohol, benzyl alcohol, $C_2$–$C_6$-ω-haloalcohols, glycolic esters, thiglycolic esters, and lactic esters. Preferably, the abovementioned alcohols are used.

The reaction is carried out in an inert solvent, for example an aromatic or aliphatic hydrocarbon such as benzene, toluene, xylene, chlorobenzene or cyclohexane, in which case the solvent can be an azeotropically boiling entrainer for the alcohol to be separated off, or, alternatively, in an excess of the compound to be reacted, which contains an OH group. If desired, the reaction can also be carried out under elevated or reduced pressure. As a rule, the reaction is carried out at a temperature of 70° C. to 180° C., preferably 100° to 150° C. Continuous removal of the liberated alcohol is advantageous for the course of the reaction.

The $C_1$–$C_3$-alkoxythiophene and the compound containing an OH group, which are to be reacted with one another, are used in a molar ratio of 1:1 to 1.5, preferably 1:1.1 to 1.3.

The reaction is carried out in the presence of a catalyst. The catalyst is an acid, in particular a protonic acid, for example $H_2SO_4$, $NaHSO_4$, $H_3PO_4$, polymeric sulfonic acid, p-toluenesulfonic acid, $HBF_4$, which in general is used in catalytic amounts of 1 to 10 moles %, relative to the alkoxythiophene. The system $NaHSO_4$ or p-toluenesulfonic acid with toluene as the solvent has proven to be particularly advantageous.

The reaction takes 30 to 300, preferably 50 to 200, minutes. By this time, the calculated amount of alcohol has been separated off. The acid catalyst is filtered off or neutralized, the solvent is separated off and the product is purified by distillation, recrystallization or chromatography.

Examples of the compounds prepared by this process are therefore:

3-ethoxythiophene, 3-propoxythiophene, 3-butoxythiophene, 3-pentyloxythiophene, 3-hexyloxythiophene, 3-heptyloxythiophene, 3-octyloxythiophene, 3-nonyloxythiophene, 3-decyloxythiophene, 3-undecyloxythiophene, 3-(n-dodecyl-2-oxy)thiophene, 3-n-dodecyl-1-oxythiophene, 3-tetradecyloxythiophene, 3-pentadecyloxythiophene, 3-hexadecyloxythiophene, 3-pentadecyloxythiophene, 3-hexadecyloxythiophene, 3-octadecyloxythiophene, 3-eicosyloxythiophene, 3-docosyloxythiophene, 3-(2'-ethylhexyloxy)thiophene, 3-(2',4',4'-trimethylpentyloxy)thiophene, 3-cyclopentyloxythiophene, 3-cyclohexyloxythiophene, 3-benzyloxythiophene, 3-propargyloxythiophene, 3-(2-chloroethyloxy)thiophene, 3-(6-chlorohexyloxy)thiophene, 3-methoxyethoxy)-thiophene, 3-(methoxyethoxyethoxy)thiophene, 3,4-diethoxythiophene, 3,4-dipropoxythiophene, 3,4-dibutoxythiophene, 3,4-dipentyloxythiophene, 3,4-dihexyloxythiophene, 3,4-dioctyloxythiophene, 3,4-dinonyloxythiophene, 3,4-didodecyloxythiophene, 3-methoxy-4-pentyloxythiophene, 3-methoxy-4-hexyloxythiophene, 3-methoxy-4-nonyloxythiophene, 3-methoxy-4-dodecyloxythiophene, 3-methyl-4-propargyloxythiophene, 3-ethoxy-4-pentyloxythiophene, 3-ethoxy-4-hexyloxythiophene, 3-butoxy-4-dodecyloxythiophene, 3-(2'-ethylhexyloxy)-4-methoxythiophene, 3-methoxy-4-methylthiophene, 3-ethoxy-4-methylthiophene, 3-methoxyethoxy-4-methylthiophene, 3-propargyloxy-4-methylthiophene, 3-butoxy-4-methylthiophene, 3-butyl-4-methoxythiophene, 3-dodecyl-4-methoxythiophene, 3-dodecyl-4-butoxythiophene, 3-butyl-4-butoxythiophene, 3,3'-dihexyloxy-2,2-dithiophene, 4,4'-didodecyloxy-2,2'-dithiophene, 3-dodecyloxy-4-methoxy-2,2'-dithiophene, glycol and methylglycol 3,4-dioxythiophene ethers, 2-butoxy-3-methoxythiophene, 2-hexyloxy-4-methoxythiophene, 2-butoxy-3-methylthiophene and 2-hexyloxy-4-methylthiophene.

Preference is given to preparing 3-hexyloxythiophene, 3-heptyloxythiophene, 3-octyloxythiophene, 3-nonyloxythiophene, 3-decyloxythiophene, 3-undecyloxythiophene, 3-dodecyloxythiophene, 3-tetradecyloxythiophene, 3-pentadecyloxythiophene, 3-hexadecyloxythiophene, 3-octadecyloxythiophene, 3-eicosyloxythiophene, 3-docosyloxythiophene, 3-(2'-ethylhexyloxy)thiophene, 3-(2',4',4'-trimethylpentyloxy)-thiophene, 3,4-dihexyloxythiophene, 3,4-dioctyloxythiophene, 3,4-dinonyloxythiophene, 3,4-didodecyloxythiophene, 3-methoxy-4-pentyloxythiophene, 3-hexyloxy-4-methoxythiophene, 3-methoxy-4-nonyloxythiophene, 3-dodecyloxy-4-methoxythiophene, 3-docosyloxy-4-methoxythiophene, 3-ethoxy-4-pentyloxythiophene, 3-ethoxy-4-hexyloxythiophene, 3-butoxy-4-dodecyloxythiophene and 3-(2'-ethylhexyloxy)-4-methylthiophene.

The thiophene ethers thus obtained can be polymerized by oxidation, for example electrochemically. The thiophenes substituted in the 2-position can be used as chain terminators for controlling the molecular weight.

In the doped form, the polymers are distinguished by good conductivity and solubility. The process allows the preparation of a series of monomeric thiophene ethers from an easily accessible starting compound, is being possible to vary the properties of the polymer prepared therefrom within wide limits, depending on the side chain.

The polymers can be employed as antistats for plastics, it being possible to obtain a solution of this polymer in the particular plastic or to adjust the thiophene polymer to the plastic by selection of a suitable side chain in the thiophene monomer or polymer.

The examples which follow illustrate the reaction according to the invention.

EXAMPLE 1

3-n-Hexyloxythiophene 20 cm³ of 3-methoxythiophene (0.2 mol) and 50 cm³ of 1-hexanol were dissolved in 30 cm³ of toluene, and 1 g of NaHSO₄ (0.01 mol) was added. The mixture was heated to 125° C. and stirred, and about 10 cm³ of a mixture of methanol and toluene were distilled off through a Vigreux column at a head temperature of 63° to 64° C., which took about 3 hours. The mixture was then washed three times with 50 cm³ of saturated NaHCO₃ solution until neutral, dried over MgSO₄ and fractionated in vacuo. After the toluene had been distilled off together with excess haxanol, 34 g of 3-n-hexyloxythiophene distilled over at 70° C. and 0.13 mbar, which corresponds to 92% of the theoretical yield. 97% pure by GC; ¹H-NMR and mass spectrum confirm the structure.

EXAMPLE 2

3-n-Nonyloxythiophene 25 cm³ of 3-methoxythiophene (0.25 mole), 50 cm³ of 1-nonanol (0.28 mol) and 30 cm³ of toluene were heated to 120° C. together with 1 g of p-toluenesulfonic acid, and about 9.5 cm³ of a methanol/toluene mixture were distilled off over a period of 3 hours. The workup was carried out as described in Example 1. Fractionation through a 30 cm Vigreux column at 0.26 mbar gave 42 g of 3-n-nonyloxythiophene of boiling point 102° to 105° C., which corresponds to 74% of the theoretical yield. ¹H-NMR and mass spectrum confirm the structure.

EXAMPLE 3

3-Dodecyloxy-4-methylthiophene 40 g of 3-methoxy-4-methylthiophene were dissolved in 120 cm³ of toluene together with 120 g of 1-dodecanol, and the solution was refluxed with 2 g of NaHSO₄. 19 ml of a methanol/toluene mixture were separated off over a period of 3 hours. The solution was washed with water until neutral, dried over MgSO₄ and subsequently fractionated. At 141° to 143° C. and 0.013 mbar, 55.6 g of 3-dodecyloxy-4-methylthiophene distilled over. 97% pure by GC, which corresponds to 63% of the theoretical yield. The substance was characterized by mass spectrum and ¹H-NMR.

EXAMPLE 4

3-Methoxyethoxy-4-methylthiophene 40 g of 3-methoxy-4-methylthiophene were dissolved in 50 cm³ of toluene with 60 cm³ of ethylene glycol monomethyl ether. 2 g of NaHSO₄ were added, the mixture was refluxed for 3 hours and 18 cm³ of a methanol/toluene mixture were removed.

Workup as in Example 3. Fractional distillation gave 29 g of 3-methoxyethoxy-4-methylthiophene, b.p. 62° to 65° C./0.2 mbar, 95% pure, which corresponds to 54% of the theoretical yield. The substance was characterized by mass spectrum and ¹H-NMR.

EXAMPLES 5 to 13

The compounds of the general formula

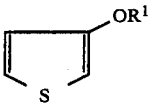

listed in the table below were prepared from 3-methoxythiophene with NaHSO₄ catalysis in the same manner as those listed in the examples; boiling points and yields are given and characterization was carried out by ¹H-NMR and mass spectra.

| Example | R¹ | B.p. °C./mbar | Yield |
|---|---|---|---|
| 5 | n-C₁₂H₂₅ | 140° C./0,26 | 75% |
| 6 | n-C₂₀H₄₂ | Chromatogr. CH₂Cl₂/SiO₂ | |
| 7 | —CH₂—CH=CH₂ | 78° C./16 | 37% |
| 8 | —CH—C≡CH | 88° C./16 | 65% |
| 9 | —CH₂—CH(CH₂)₃CH₃ with CH₂CH₃ | 88° C./0,13 | 50% |
| 10 | -Cyclohexyl | 66° C./0,06 | 38% |
| 11 | —CH₂—CH₂—Cl | 65–68° C./0,13 | 30% |
| 12 | —CH₂—CH₂—OCH₃ | 53° C./0,13 | 46% |
| 13 | —CH₂—C₆H₅ | 99° C./0,26 | 62% |

EXAMPLE 14

2-Hexyloxythiophene 15 cm³ of 2-methoxythiophene were dissolved in 40 cm³ of n-hexanol and 30 cm³ of toluene, 1 g of NaHSO₄ was added, and the mixture was refluxed for several hours. After distilling off 6 cm³ of an azeotrope of methanol and toluene, the residue was washed with sodium carbonate solution, dried and fractionated. 18 g of 2-hexyloxythiophene of b.p. 66° C./0.26 mbar were distilled off, 96% pure. Yield 65% of theory.

EXAMPLE 15

3-Hexyloxy-4-butylthiophene 10 g of 3-methoxy-4-butylthiophene, prepared from 3-bromo-4-butylthiophene by reaction with sodium methylate in methanol with catalysis by CuO, b.p. 54° C./0.26 mbar, were dissolved as in Example 14 in 50 cm³ of 1-hexanol and 30 ml of toluene, and 1 g of NaHSO₄ was added. After distilling off 6 cm³ of azeotrope, the batch was worked up as in Example 14. Yield 8.5 g of 3-hexyloxy-4-butylthiophene of b.p. 112° to 116° C./0.26 mbar, which corresponds to 60% of theory.

EXAMPLE 16

3-Methoxy-4-hexyloxythiophene 10 g of 3,4-dimethoxythiophene were dissolved in 10 cm³ of 1-hexanone and 30 cm³ of toluene, 0.5 g of NaHSO₄ was added, and the mixture was heated to reflux. 6 cm³ of azeotrope were distilled off and the batch was then worked up as in Example 14. Fractionation gave 3.7 g of 3-methoxy-4-hexyloxythiophene, b.p. 80° to 85° C./0.1 mbar. 4 g of dihexyloxythiophene were obtained from the distillation residue by chromatography through SiO₂ using CH₂Cl₂.

EXAMPLE 17

6-Chlorohexyloxythiophene 26 cm$^3$ of 6-chloro-1-hexanol and 1 g of p-toluenesulfonic acid were added to 20 cm$^3$ of 3-methoxythiophene in 30 cm$^3$ of toluene, and the mixture was refluxed. 9.2 cm$^3$ of a toluene/methanol azeotrope were distilled off. After neutralization with aqueous sodium carbonate solution, 14 g of 6-chloro-hexyloxythiophene were obtained by fractionation, b.p. 87° C./0.01 mbar, 98% pure.

I claim:

1. A thiophene ether of the formula I

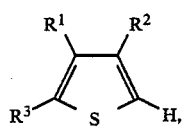

in which
  R$^1$ denotes a straight-chain or branched C$_7$–C$_{18}$-alkoxy radical, a C$_4$–C$_{18}$alkenyloxy radical, a C$_3$–C$_{12}$-alkynyloxy radical, a C$_5$–C$_6$-cycloalkoxy radical, a phenyl-C$_1$–C$_4$-alkoxy radical, a radical of the formula II

   (II)

in which n is 2 to 6 and X denotes a halogen atom, a hydroxyl, carboxylic ester, —SO$_3$Me (Me is an alkali metal or —N$^+$R$_4^5$ where R$^5$ is H or alkyl), nitro, cyano, carboxamide, —OCH$_3$, —OC$_2$H$_5$ or —(OCH$_2$Ch$_2$)$_m$— OCH$_3$ group where m is 1 to 3, a quaternary ammonium group or a —P(O)(OR$^4$)$_2$ group where R$^4$ is H or C$_1$–C$_4$-alkyl, or denotes a radical of glycolic acid, thioglycolic acid, lactic acid or the ester of these acids,
  R$^2$ denotes R$^1$ or a hydrogen atom, a C$_1$–C$_{12}$-alkyl group or an aryl radical,
  R$^3$ denotes a hydrogen atom, a C$_1$–C$_6$-alkyl group or a C$_4$–C$_6$-alkoxy group.

2. A process for the preparation of thiophene ethers of the formula I

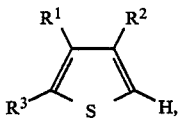

in which
  R$^1$ denotes a straight-chain or branched C$_1$–C$_{18}$-alkoxy radical, a C$_3$–C$_{18}$-alkenyloxy radical, a C$_3$–C$_{12}$-alkynyloxy radical, a C$_5$–C$_6$-cycloalkoxy radical, a phenyl-C$_1$–C$_4$-alkoxy radical, a radical of the formula II

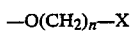   (II)

in which n denotes 2 to 6 and X denotes a halogen atom, a hydroxyl, carboxylic ester, —SO$_3$Me (Me is an alkali metal or —N$^+$R$_4^5$ where R$^5$ is H or alkyl), nitro, cyano, carboxamide, —OCH$_3$, —OC$_2$H$_5$ or —(OCH$_2$CH$_2$)$_m$— OCH$_3$ group where m is 1 to 3, a quaternary ammonium group or a —P(O)(OR$^4$)$_2$ group where R$^4$ is H or C$_1$–C$_4$-alkyl, or denotes a radical of glycolic acid, thioglycolic acid, lactic acid or the ester of these acids,
  R$^2$ denote R$^1$ or a hydrogen atom, a C$_1$–C$_{12}$-alkyl group or an aryl radical,
  R$^3$ denotes a hydrogen atom, a C$_1$–C$_6$-alkyl group or a C$_4$–C$_6$-alkoxy group, which comprises heating a 2-, 3-, 2,3-, 2,4- or 3,4-C$_1$–C$_3$-alkoxythiophene together with a compound containing an OH group of the formula

   (III)

in which R$^1$ has the abovementioned meaning, in the presence of an acid catalyst in an amount of 1 to 10 moles %, relative to the amount of the alkoxythiophene, for 50 to 300 minutes to a temperature of about 100° to 150° C. and separating off the resulting C$_1$–C$_3$-alcohol, wherein the acid catalyst is H$_2$SO$_4$, NaHSO$_4$, H$_3$PO$_4$, HBF$_4$, p-toluene-sulfonic acid or a polymeric sulfonic acid.

3. The process as claimed in claim 2, wherein the acid catalyst is NaHSO$_4$ or p-toluenesulfonic acid.

4. The process as claimed in claim 2, wherein the resulting C$_1$–C$_3$-alcohol is separated off by azeotropic distillation.

5. The process as claimed in claim 4, wherein said distillation is carried out during the reaction so as to provide continuous removal of the resulting C$_1$–C$_3$ alcohol.

6. The process as claimed in claim 2, wherein the reaction is carried out in toluene as the solvent.

7. The process as claimed in claim 2, wherein the acid catalyst is NaHSO$_4$ or p-toluenesulfonic acid, and the said heating is carried out for 50 to 200 minutes.

8. The process as claimed in claim 7, wherein the resulting C$_1$–C$_3$ alcohol is continuously removed by azeotropic distillation during the said heating step.

* * * * *